(12) United States Patent
Von Falkenhausen et al.

(10) Patent No.: US 7,029,549 B1
(45) Date of Patent: Apr. 18, 2006

(54) METHOD AND DEVICE FOR DISPENSING ADHESIVE LAMINATE SEGMENTS

(75) Inventors: Christian Von Falkenhausen, Meckenheim (DE); Klaus Schumann, Neuwied (DE); Peter Steinborn, Neuwied (DE); Frank Theobald, Bad Breisig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 478 days.

(21) Appl. No.: 10/089,187

(22) PCT Filed: Sep. 13, 2000

(86) PCT No.: PCT/EP00/08927

§ 371 (c)(1),
(2), (4) Date: Sep. 12, 2002

(87) PCT Pub. No.: WO01/22946

PCT Pub. Date: Apr. 5, 2001

(30) Foreign Application Priority Data

Sep. 28, 1999 (DE) .............................. 199 46 384

(51) Int. Cl.
  *B32B 31/00* (2006.01)
  *B44C 1/00* (2006.01)
  *B65G 59/00* (2006.01)

(52) U.S. Cl. ..................... 156/248; 156/230; 156/270; 156/523; 156/540; 221/1

(58) Field of Classification Search ............... 156/152, 156/230, 235, 238, 239, 240, 250, 258, 252, 156/257, 259, 277, 344, DIG. 28, DIG. 33, 156/DIG. 38, 231, 247–249, 269–271, 510, 156/516, 523, 538–543; 221/1, 25, 26, 33, 221/30

See application file for complete search history.

(56) References Cited

U.S. PATENT DOCUMENTS

| | | | |
|---|---|---|---|
| 3,006,502 A | | 10/1961 | Tobey |
| 3,694,287 A | * | 9/1972 | Marshall ..................... 156/257 |
| 4,475,969 A | * | 10/1984 | Reed ........................... 156/152 |
| 4,648,930 A | * | 3/1987 | La Mers ...................... 156/247 |
| 5,304,264 A | * | 4/1994 | Wehrmann ................... 156/64 |
| 5,849,143 A | * | 12/1998 | Ingalls ........................ 156/556 |
| 5,938,890 A | * | 8/1999 | Schlinkmann et al. ...... 156/541 |
| 6,123,796 A | * | 9/2000 | Kathmann et al. .......... 156/249 |
| 6,334,921 B1 | * | 1/2002 | Duschek ...................... 156/230 |
| 6,571,983 B1 | * | 6/2003 | Schumann et al. ........... 221/25 |
| 6,758,254 B1 | * | 7/2004 | Moore et al. ................ 156/540 |

FOREIGN PATENT DOCUMENTS

WO   97 22315 A   6/1997

* cited by examiner

*Primary Examiner*—Sue A. Purvis
(74) *Attorney, Agent, or Firm*—Birch, Stewart, Kolasch & Birch, LLP

(57) ABSTRACT

A process for dispensing pressure-sensitive adhesive laminates (3) or laminate sections from a movable primary (1) onto a movable secondary carrier band (2), the laminates (3), upon deflection of the primary band (1) around a dispenser edge (4), being detached and dispensed onto the secondary band (2), is characterized in that the primary band (1) is provided with at least one separation line or predetermined breaking line, thus subdividing it into at least two strips (5, 5'), and that the strips are individually drawn from separate sections (4', 4'') of the dispenser edge (4).

19 Claims, 3 Drawing Sheets

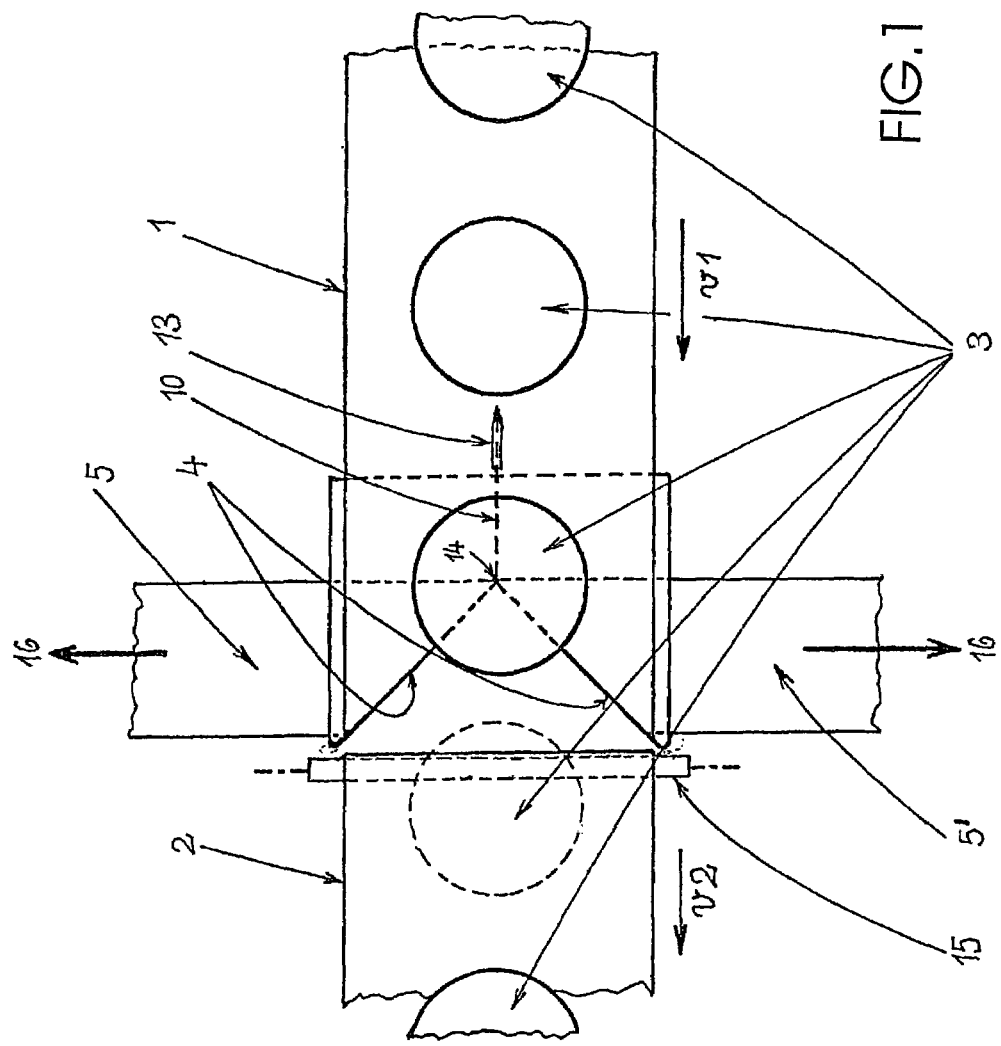
FIG.1
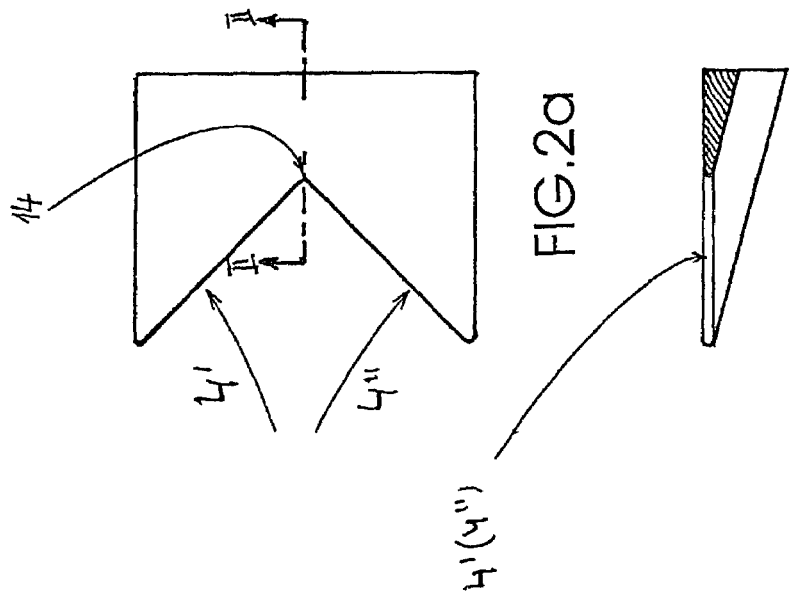
FIG.2a
FIG.2b

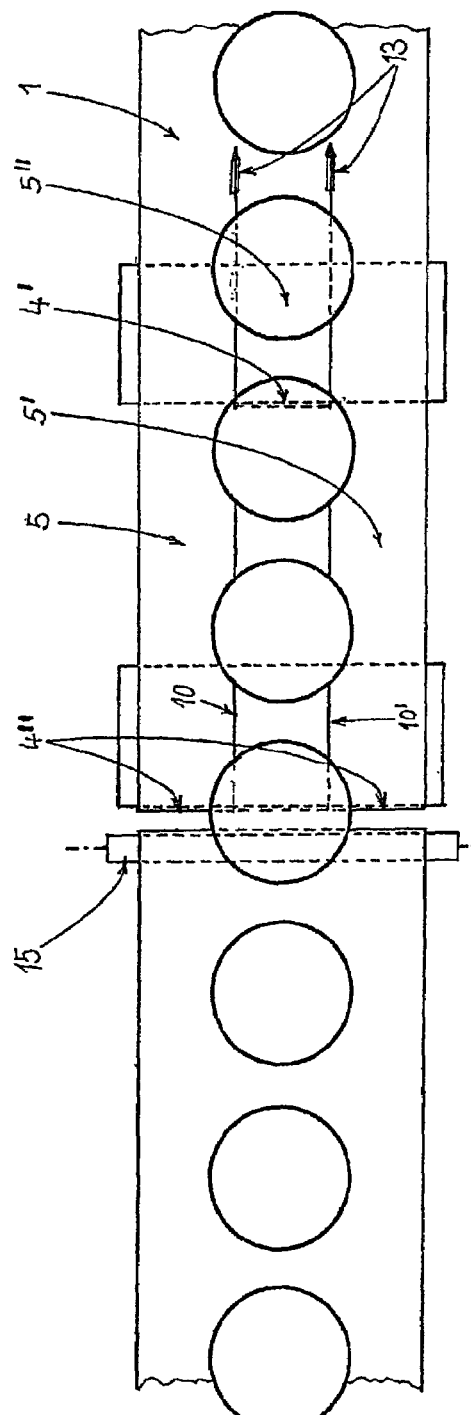
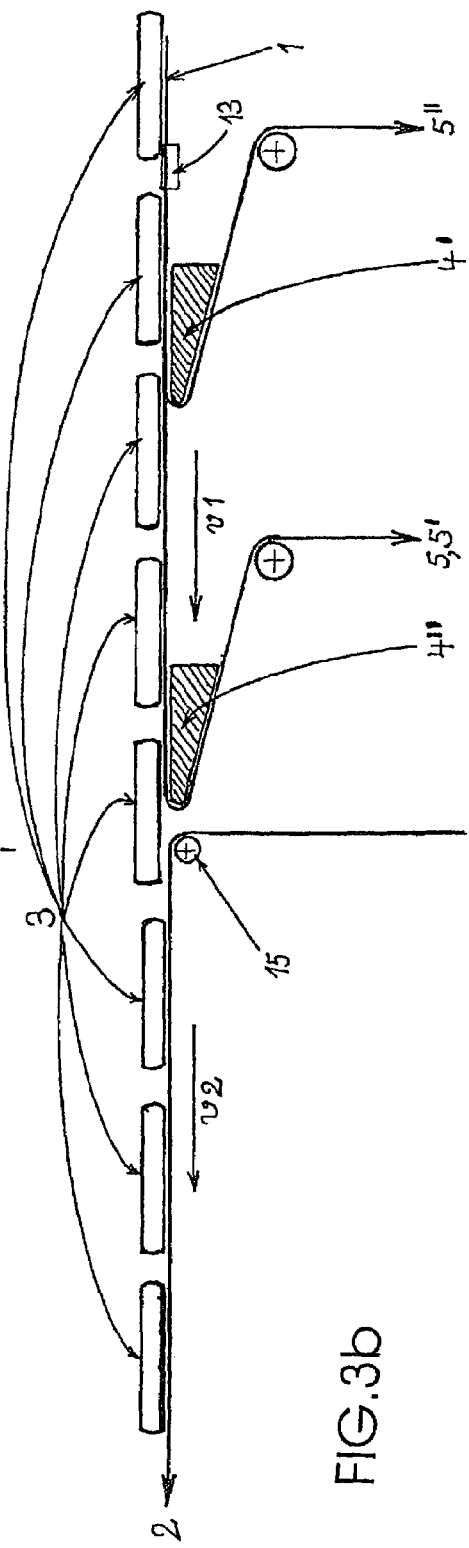
FIG.3a
FIG.3b

Plan View

Front View

METHOD AND DEVICE FOR DISPENSING ADHESIVE LAMINATE SEGMENTS

BACKGROUND OF THE INVENTION

1. Field of the Invention

Process and device for dispensing pressure-sensitive adhesive laminate sections from a movable primary onto a movable secondary carrier band.

2. Description of the Related Art

The invention relates to a process for dispensing pressure-sensitive adhesive laminates or laminate sections from a movable primary to a movable secondary carrier band, said laminates, upon deflection of the primary band around a dispenser edge, being detached and dispensed onto the secondary band.

It is known how to produce and use pressure-sensitive adhesive laminate sections which are adhesive over a surface. These may be, for example, labels, stickers, transdermal therapeutic systems (TTSs) or double-sided adhesive tape. The pressure-sensitive adhesive surface or a pressure sensitive adhesive-rendered matrix of these laminate sections is typically covered by a carrier band at least partially projecting beyond the same. Technically, these laminate sections are fabricated by punching a matrix and a backing layer, which is connected thereto, down to the carrier web by means of an appropriate tool, and peeling off and discarding a projecting lattice of matrix and a backing layer.

With this kind of fabrication of dermal or transdermal therapeutic, pressure-sensitive adhesive laminate sections, the surface coating of the carrier band may become damaged upon punching through the matrix and a backing layer connected with the matrix, which in the case of prolonged storage will cause problems in releasing the matrix from the carrier layer, especially where the therapeutic system possesses a strong tendency for cold flow, enabling the matrix to unintentionally form a pressure-sensitive adhesive bond with the carrier layer, which carrier layer has not been rendered adhesive.

This problem can, however, be avoided by transferring the transdermal plasters, following the separation of the sections of the laminate by punching them out of an original laminate, to a final, secondary carrier layer. A corresponding process is described in WO 97/22315. This process has as a prerequisite that a transdermal therapeutic system which is to be transferred can be released from a primary carrier band when being guided around a dispenser edge, and can thus be transferred to the final, secondary carrier band. If, however, the adhesive force of the matrix exceeds a certain value, this method can no longer be applied as the pressure-sensitive adhesive matrix in this case is no longer detachable from the carrier band but is deflected along with the primary carrier band.

In known dispensing methods, such as described, for instance, in WO 97/22315, the primary carrier band, with the segregated laminate sections, e.g. plasters, is guided in the direction of conveyance over a dispensing edge, the plaster in the process being peeled from the carrier band along the entire width of the plaster. The peeling process here takes place in the direction of the band. If the adhesion of the plaster to the primary carrier layer is very strong, this may, even in the case of a very acute dispensing angle, cause the plaster to be pulled around the edge along with the primary carrier layer without becoming detached therefrom, thus making a dispensing process impossible.

SUMMARY OF THE INVENTION

Starting from the prior art, it is the object of the present invention to indicate a process and a device for dispensing pressure-sensitive adhesive laminates or laminate sections from a movable primary onto a movable secondary carrier band, which overcome the difficulties and technical limitations mentioned and which are readily suitable for detaching even strongly pressure-sensitive adhesive laminate sections from their carrier bands upon deflecting the said sections around a dispenser edge, and for dispensing the said sections onto a movable secondary carrier band.

This object is solved by the invention, in a process form dispensing pressure-sensitive adhesive laminates or laminate sections from a movable primary onto a movable secondary carrier band, by separating the primary band into at least two strips or providing the primary band with corresponding predetermined breaking lines, deflecting the strips individually at the dispenser edge, and, in the process, detaching the pressure-sensitive adhesive laminates from the strips and dispensing them onto the secondary band.

An essential embodiment of the process of the invention provides for the dispenser edge to be designed such that the at least two strips of the first carrier band are deflected each at its own section of the dispensing edge. In the simplest case, the dispenser edge thus has two sections, at each of which is deflected a respective strip—preferably in different directions. To this end, the two sections of the dispenser edge are arranged in a non-linear manner. Between the two sections of the dispenser edge there is an angle, which is between 1° to 179°, or 181° to 359°. The separation line, or the predetermined breaking line, between the two strips of the first carrier band in this case runs precisely over the point of intersection of the two sections of the dispensing edge.

By subdividing the primary band into at least two strips which are pulled from the dispenser edge individually, there results, during the dispensing process, a stabilisation of the plaster in the direction of the band. This is promoted, in the case of a non-linear design of the dispenser edge, by the fact that the strips are pulled off to one or both sides not in the direction of band travel, but each at an angle to the direction of band travel.

An alternative embodiment of the process, wherein the primary band is divided into at least three strips (i.e. by at least two separating or predetermined breaking lines), is characterized in that initially the inner strip or strips of the primary band are deflected at a first section of the dispenser edge and are, in the process, peeled off from the primary band and the laminates still adhering thereto. In this process, the pressure-sensitive adhesive laminates continue to be connected with the outer strips of the primary band. The outer strips are subsequently deflected via further sections of the dispenser edge, the pressure-sensitive adhesive laminates finally being released and dispensed onto the secondary band.

Due to the fact that each strip of the primary carrier web covers only a partial portion of the pressure-sensitive adhesive surface of the laminate section, which section as a consequence needs to overcome only a fraction of the total pressure-sensitive adhesive force, the detachment of the strongly pressure-sensitive adhesive laminate sections can be accomplished strip by strip, simultaneously, or successively in several stages, without any difficulty.

Since, especially in the case of successive detachment, only a fraction of the pressure-sensitive adhesive force needs to be overcome at a time, it is also possible in the process according to the invention to make use of the measure of guiding the primary carrier band at a slower transport rate relative to the secondary carrier band. This enables, for instance, the late placement, or adhesion, of a pressure-sensitive adhesive laminate section onto the secondary band, with only a small portion still sticking to the primary carrier web. In this way, it is possible to realise substantial differences in band speed between the primary and secondary bands, thereby enabling an increase in the distances between the individual systems without taking further measures. The dispensing process may be accomplished in continuous or intermittent operation.

A device for the transfer of pressure-sensitive adhesive laminates or laminate sections from a movable primary to a movable secondary carrier band, with the laminates, upon deflection of the primary band around a dispenser edge being detached and being dispensed onto the secondary band, and comprising a primary and a secondary carrier band and a dispenser edge, is characterized in that it has at least one separating means arranged such that the primary band is provided with at least one separation and/or predetermined breaking line during movement of the said band in the direction of travel.

In a further embodiment, the process can be accomplished in cycles, whereby the dispenser edge (4) is moved, with the aid of its own drive, in the direction of band travel (the so-called advance travel) in a first cycle, and during or after the dispensing of the pressure-sensitive adhesive laminates (3) or laminate sections is moved against the direction of band travel (the so-called return travel) back to the start position in a further cycle.

Further embodiments of the device are also indicated.

BRIEF DESCRIPTION OF THE DRAWINGS

Further details, features and advantages of the invention will become apparent from the following explanation of two examples of embodiments schematically represented in the drawings. The drawings show:

FIG. 1: a plan view of the device;

FIG. 2a: a plan view of a dispenser edge with non-linear configuration, with the two sections (4' and 4") forming an angle of 90°;

FIG. 2b: a sectional view of the dispenser edge cut along the section plane 11—11 in FIG. 2a;

FIG. 3a: a plan view of a further embodiment of the dispensing device, wherein a middle section 4' is arranged in the direction of travel at a distance from two further sections 4";

FIG. 3b: a side view of the dispensing device according to FIG. 3a; and

DETAILED DESCRIPTION

Figure 4:
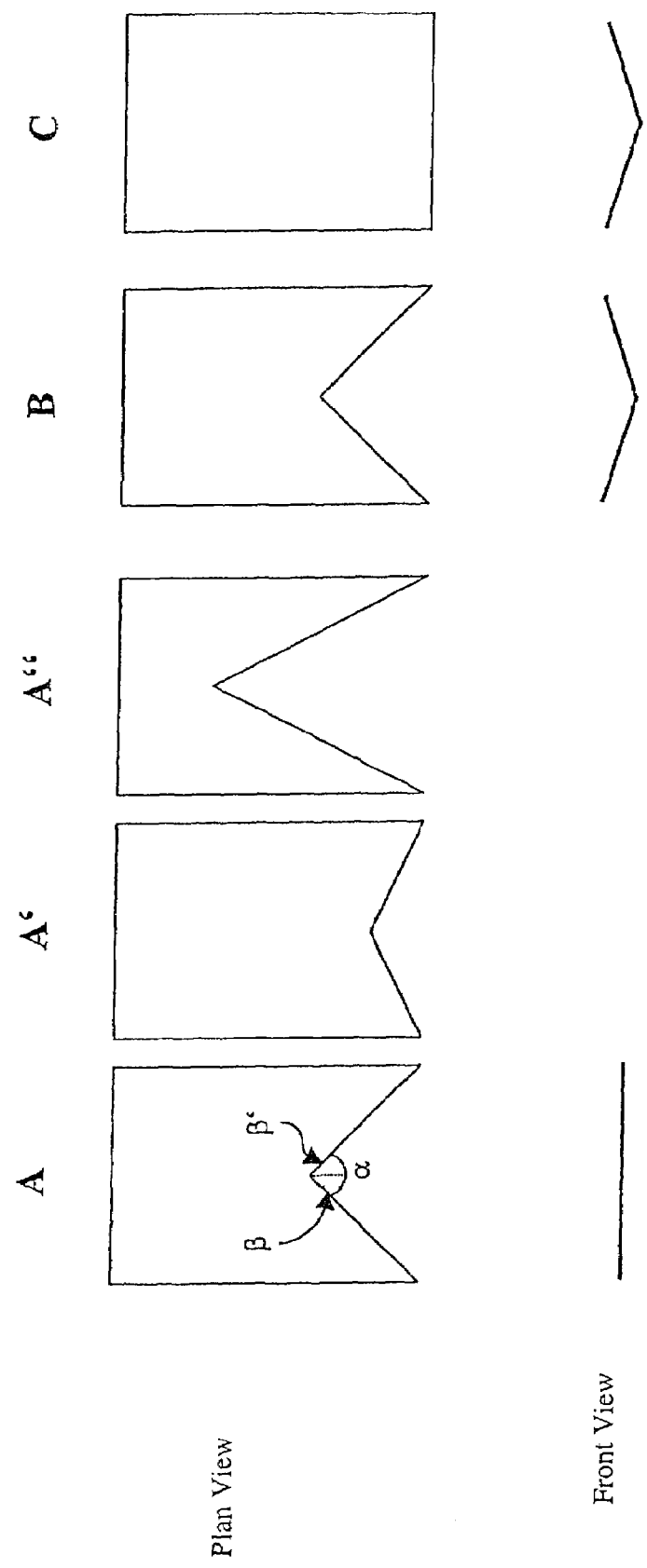
FIG. 4: dispensing edge shapes.

The process for dispensing pressure-sensitive adhesive laminates 3 or laminate sections from a movable primary carrier band 1 to a movable secondary carrier band 2, with the laminates 3, upon deflection of the primary band 1 around a dispenser edge 4, being detached and being dispensed onto the secondary band 2, will become clear from viewing the FIGS. 1 to 3b together and is characterized by the fact that the primary band 1 is divided into at least two strips 5, 5', the strips are deflected individually at the dispenser edge 4 and the laminates 3 are, in the process, removed from the strips 5, 5' and dispensed onto the secondary band 2.

This secondary band 2 can be advanced from underneath the band towards the discharge side of the primary band 1 via at least one deflecting roll 15.

As can be seen from FIG. 1, the band velocities V1 and V2, may be different, that is, V2 can be moved more slowly or more rapidly than V1. The distances between the laminate sections 3, which are to be dispensed, thereby become smaller or larger. The band velocities V1 and V2 may, however, also be equal.

According to the invention, the primary band 1 is separated into at least two strips, 5, 5' and the strips are singly deflected at the separate sections of the dispenser edge 4, the laminates 3 being removed from the strips 5, 5' and dispensed onto the secondary band 2.

As an aspect essential to the invention, the dispenser edge 4 possesses at least two sections 4' and 4". These sections 4' and 4" may form an angle of between 1° to 179° and 181° to 359°. The apex 14 here represents the point of intersection of the two non-linearly arranged sections 4' and 4" of the dispenser edge. The separation or predetermined breaking line 10 runs precisely over this point 14.

Preferred angles are those between 5° and 175°, particularly preferred are angles from 30° to 150°, and more particularly 90°.

To this end, as can be seen from FIGS. 3, 3b, there is arranged in the region of the primary band 1 at least one separating means 13, in such a manner that the primary band 1 is split, weakened or perforated, but not the pressure-sensitive adhesive laminate 3 or the laminate sections.

One embodiment of the process, wherein the dispenser edge 4 in non-linear and the primary band 1 is separated into two strips, is characterized in that the strips 5, 5' are drawn off, not in the direction of travel of the primary band 1, but, as can be seen from FIG. 1, each at an angle to the direction of travel of the primary band 1, towards both sides. In the example shown in FIG. 1, the dispenser edge 4 has two sections at an angle of 90°, whereby the two strips 5, 5' are being pulled off each at a right angle from the direction of band travel, towards both sides, as indicated by the arrows 16.

The shape of the dispenser edge 4, in plan view and in section, is apparent from FIGS. 2a and 2b.

FIGS. 3a and 3b show another embodiment of the process using a device suitable therefor, in plan view (FIG. 3a) and in side view (FIG. 3b). Here, the primary web 1 is continuously separated into three strips 5, 5', 5", which may be of equal or different width. In the direction of travel of the band, the inner strip 5" of the primary band 1 is initially directed over a first section of the dispenser edge 4' and, in the process, is pulled off from the primary band 1 and from the laminates 3, which remain on the primary band 1. The pressure-sensitive adhesive laminates 3 continue to be pressure-sensitive-adhesively connected with outer strips 5, 5' of the primary band 1. Subsequently, the outer strips 5, 5' of the primary web are guided over further sections of the dispenser edge 4", the laminates 3 are detached in the process and are dispensed onto the secondary band 2. Here, too, the dispenser edge has non-linearly arranged sections 4' and 4". Since, however, the two sections 4' and 4" are arranged at a distance in the direction of the band, it is not necessary for the sections to form an angle not equal to 0°.

The primary band 1 is thus successively peeled from the pressure-sensitive adhesive laminate 3 in several stages. Finally, the primary support band 1 may be guided at a different speed from that of the secondary carrier band 2, especially at a lower transport speed.

A device for transferring pressure-sensitive adhesive laminates or laminate sections 3 from a movable primary 1 to a movable secondary carrier band 2, with the laminates 3, upon deflection of the primary band 1 around a dispenser edge 4, being detached and dispensed onto the secondary band, will become clear when viewing the figures together and comprises a primary 1 and a secondary carrier web 2, at least one dispenser edge 4 and at least one separating means. The separating means may be in the form of a fixedly positioned cutting blade 13 pressing against the primary band 1. It may be configured and arranged such that, during the movement of the primary band 1 in the direction of travel, it separates the primary band 1 lengthwise into at least two strips 5, 5', preferably in the middle region. The separating means may, however, also be a rotating cutting roller, that is, a so-called rotating knife. The separating means may split the carrier band completely, but may also project only partially into said band, thus creating a line of weakening (predetermined breaking line). Finally, the line may also be configured as a perforation if the primary band is to be split or cut off only point-wise or section-wise.

One embodiment of the device provides for a middle strip 51, or at least two inner strips 5 to be narrower than the laminate 3 to be detached.

A further embodiment of the invention provides for a first section 4' of the dispenser edge 4, which section is arranged at a middle region, and further sections 4" of the dispenser edge 4, which sections are arranged in the outer region, to be configured at right angles to the direction of band travel, as can be clearly seen form FIG. 3a.

If the dispenser edges are arranged obliquely to the direction of band travel, it is also possible to make use of the measure of providing the V-shaped profile of the dispenser edge 4 with at least one step at both sides of cutting lines (10, 10') which extend in the direction of band travel.

Finally, the dispenser edge 4 need not be configured so as to be planar, but instead may have an inwardly facing fold around a folding line, which folding line extends in the direction of band travel. Here, the position of the at least one fold line preferably corresponds to the position of the at least one separation or predetermined breaking line.

As can be seen from FIGS. 2a and 2b, it is preferred that, downstream of the dispensing edge 4, the secondary carrier band 2 be forwarded in the direction of band travel to the transfer site via a deflecting device in the form of a roller 15 or some kind of rounded deflecting edge.

The dispensing edge may be configured in the shapes indicated in FIG. 4. The V-shaped cut of the dispenser edge may be configured in an obtuse (A') or acute (A") angle. The angle α (FIG. 4) can vary between 5° and 175°. Advantageously, however, an angle of 300 to 1500, and particularly advantageously, of 90°, is observed. Embodiments where the angles β and β' are configured so as to be asymmetric may be of advantage here.

The dispensing edge itself may be configured so as to be planar (A), but embodiments are also conceivable where a non-planar dispenser edge (FIGS. 4B and 4C; front view) is of particular advantage. In this case, it is advantageously possible to dispense with a V-shaped configuration of the dispenser edge. Here, the pressure-sensitive adhesive laminate section is stabilised in the third dimension by a fold.

The invention is useful and provides an optimal solution to the task set at the beginning.

What is claimed is:

1. A process for dispensing pressure-sensitive adhesive laminates (3) or laminate sections from a movable primary (1) onto a movable secondary carrier band (2), the laminates (3), upon deflection of the primary band (1) around a dispenser edge (4), being detached and dispensed onto the secondary band (2), comprising providing the primary band (1) with at least one separation line or predetermined breaking line, thus subdividing it into at least two strips (5, 5'), and that the strips are individually pulled from separate sections (4', 4") of the dispenser edge, and the dispenser edge (4) is moved, in a first cycle, in the direction of travel of the band, and, during or after dispensing of the pressure-sensitive adhesive laminates (3) or laminate sections, is returned, against the direction of travel of the band, to the start position in a further cycle.

2. The process according to claim 1, wherein the at least two sections of the dispenser edge (4) are arranged in a non-linear manner.

3. The process according to claim 1, wherein the two sections (4', 4") of the dispenser edge 4 span an angle of between 1° to 179° or 181° to 359°.

4. The process according to claim 1, wherein the two sections (4', 4") of the dispenser edge are arranged at a distance from each other in the direction of travel of the band.

5. The process according to claim 1, with the primary band (1) being separated into at least three strips (5, 5', 5"), wherein initially the inner strip or strips (5") of the primary band (1) is/are deflected at a first section of the dispenser edge (4), and that the outer strip (5, 5') is subsequently deflected at further sections of the dispenser edge (4).

6. The process according to claim 1, wherein the at least two strips of the primary band (1) are peeled from the pressure-sensitive adhesive laminate (3) successively, in several stages.

7. The process according to claim 1, wherein the at least two strips of the primary band (1) are simultaneously peeled from the pressure-sensitive adhesive laminate (3).

8. The process according to claim 1, wherein the primary band (1) is directed, relative to the secondary carrier band (2), at a transport speed which is equal to or lower than that of the secondary carrier band (2).

9. The process according to claim 1, wherein the primary band (1) and/or the secondary band (2) is/are conveyed continuously or intermittently.

10. A device for dispensing pressure-sensitive adhesive laminates (3) or laminate sections from a movable primary (1) onto a movable secondary carrier band (2), said laminates (3), upon deflection of the primary band (1) around a dispenser edge (4), being detached and dispensed onto the secondary band (2), comprising a primary (1) and a secondary carrier band (2) and a dispenser edge (4), wherein the device has a separation means which is arranged such that the primary band (1) during its movement in the direction of travel, is provided with at least one separation or predetermined breaking line.

11. The device according to claim 10, wherein the separating means is a stationary knife, a rotating cutting roller or a rotating knife.

12. The device according to claim 10, wherein the dispenser edge (4) has at least two sections (4', 4") in non-linear arrangement.

13. The device according to claim 10, wherein at least two sections (4', 4") form an angle of between 1° to 179° or 181° to 359°.

14. The device according to claim 10, wherein the at least two sections (4', 4") are arranged at a distance from each other, in the direction of travel of the band.

15. The device according to claim 10, wherein a separation or predetermined breaking line runs in the primary band (1), exactly over the end points of the sections of the dispenser edge.

16. The device according to claim 10, wherein a first section of the dispenser edge (4), which section is arranged in a middle region, and further sections of the dispenser edge (4), which sections are arranged in the outer region, are configured at right angles to the direction of travel of the band.

17. The device according to claim 10, wherein the V-shaped profile of a dispenser edge (4) has at least one step on both sides of the cutting lines (10, 10'), which run in the direction of travel of the band.

18. The device according to claim 10, wherein the dispenser edge (4) has an inwardly facing fold in the direction of travel of the band.

19. The device according to claim 10, wherein, downstream of the dispensing edges 4, the secondary carrier band (2) is advanced in the direction of band travel to the transfer site via a deflecting device in the form of a roller (15) or a rounded deflecting edge.

* * * * *